(12) United States Patent
Dutta et al.

(10) Patent No.: US 8,471,068 B2
(45) Date of Patent: Jun. 25, 2013

(54) PROCESS FOR THE PREPARATION OF 4-(4-HYDROXYPHENYL)BUTAN-2-ONE USING SOLID ACID CLAY CATALYST

(75) Inventors: Dipak Kumar Dutta, Jorhat (IN); Madan Gopal Pathak, Jorhat (IN)

(73) Assignee: Council of Scientific and Industrial Research, New Delhi (IN)

( * ) Notice: Subject to any disclaimer, the term of this patent is extended or adjusted under 35 U.S.C. 154(b) by 90 days.

(21) Appl. No.: 12/934,568

(22) PCT Filed: Mar. 16, 2009

(86) PCT No.: PCT/IN2009/000178
§ 371 (c)(1),
(2), (4) Date: Jul. 8, 2011

(87) PCT Pub. No.: WO2009/118755
PCT Pub. Date: Oct. 1, 2009

(65) Prior Publication Data
US 2011/0257439 A1  Oct. 20, 2011

(30) Foreign Application Priority Data
Mar. 26, 2008 (IN) .............................. 772/DEL/2008

(51) Int. Cl.
*C07C 45/61* (2006.01)
*B01J 21/16* (2006.01)

(52) U.S. Cl.
USPC .......................................... 568/315; 502/83

(58) Field of Classification Search
USPC .......................................... 568/315; 502/83
See application file for complete search history.

(56) References Cited

U.S. PATENT DOCUMENTS
5,908,770 A  6/1999  Joulain et al. ................. 435/148

FOREIGN PATENT DOCUMENTS
DE  2145308       3/1973
EP  0 702 596    12/1996
WO  WO 95/14530   6/1995

OTHER PUBLICATIONS

Borejsza-Wysocki et al., "(p-Hydroxyphenyl)butan-2-one levels in raspberries determined by chromatographic and organoleptic methods," *J Food Chem*, 40(7):1176, 1992.
Krishan et al., "Liquid phase alkylation of phenol with 4-hydroxybutan-2-one in the presence of modified zeolite HBEA," *Appl. Cata. A: General*, 241:247-260, 2003.
Laszlo and Mathy, "Catalysis of *Friedel-Crafts* Alkylation by a Montmorillonite Doped with Transition-Metal Cations," *Helvetica Chimica Acta*, 70:577-586, 1987.
Mendioroz et al., "Texture Evolution of Montmorillonite under progressive acid treatment: change from H3 to H2 type of hysteresis," *Langmuir*, 3:676-681, 1986.
Kosjek et al., "Efficient production of raspberry ketone via 'green' biocatalytic oxidation," *Tetrahedron*, 59:9517-9521, 2003.
Schinz et al., "[Aromatic materials. I. Raspberry aromatic materials]" *Helv. Chim. Acta.* 40:1839-59, 1957. (English abstract of German publication).
Teteiwa et al., "Cation-exchanged montmorillonite-catalyze facile friedel-crafts alkylation of hydroxy and methoxy aromatics with 4-hydroxbutan-2-one to produce raspberry ketone and some pharmaceutically active compounds," *Journal of Organic Chemistry*, 59:5901-5904, 1994.

*Primary Examiner* — Sikarl Witherspoon
(74) *Attorney, Agent, or Firm* — Fulbright & Jaworski L.L.P.

(57) ABSTRACT

Solid acid catalyst such as acid activated-Montmorillonite clay composite has been developed by modifying the Na-Montmorillonite clay with acid (HCl) treatment for different periods such as 5 minutes to about 4 hours and activating at about 120° C. for about 2 hours. Friedel Crafts alkylation reaction between phenol and 4-hydroxybutan-2-one in presence of the acid activated Montmorillonite clay catalysts exhibiting layered clay structures (basal spacing $d_{001}$ ranging from about 10 to 13.5 Å), high surface area (250-400 m$^2$/g), highly porous {micropores in the range 5 to 15 Å and mesopores in the range 30 to 80 Å}, average pore volume 0.2 to 0.65 cc/g, and surface acidity in the range 0.4-0.6 mmol/g; under constant stirring and at pressure of 1-15 bar, temperature 100-150° C. for a period of about 12-24 hours produces 4-(4-hydroxyphenyl)butan-2-one (Raspberry ketone) exhibiting conversion about 35-55% and high selectivity in the range 75-81%.

11 Claims, No Drawings

PROCESS FOR THE PREPARATION OF 4-(4-HYDROXYPHENYL)BUTAN-2-ONE USING SOLID ACID CLAY CATALYST

This application is a national phase application under 35 U.S.C. §371 of International Application No. PCT/IN2009/000178 filed 16 Mar. 2009, which claims priority to Indian Patent Application No. 772/DEL/2008 filed 26 Mar. 2008. The entire text of each of the above-referenced disclosures is specifically incorporated herein by reference without disclaimer.

FIELD OF THE INVENTION

The present invention provides an ecofriendly process for the preparation of 4-(4-hydroxyphenyl)butan-2-one by selective alkylation of phenol with 4-hydroxybutan-2-one in presence of solid acid catalyst.

The present invention particularly relates to a process for Friedel-Crafts alkylation of phenol with 4-hydroxybutan-2-one to produce 4-(4-hydroxyphenyl)butan-2-one catalysed by acid activated clay catalyst. The invention more particularly relates to an improved process of alkylation of phenol with 4-hydroxybutan-2-one to produce 4-(4-hydroxyphenyl)butan-2-one catalysed by acid activated Montmorillonite clay catalyst. The invention still more particularly relates to an improved process of alkylation of phenol with 4-hydroxybutan-2-one to produce 4-(4-hydroxyphenyl)butan-2-one selectively catalysed by acid activated Montmorillonite clay catalyst. The invention still more particularly relates to an improved process of alkylation of phenol with 4-hydroxybutan-2-one to produce 4-(4-hydroxyphenyl)butan-2-one catalysed by eco-friendly and recyclable acid activated Montmorillonite clay catalyst.

BACKGROUND OF THE INVENTION

The compound 4-(4-hydroxyphenyl)butan-2-one also known as Raspberry ketone exhibits its characteristic raspberry odour and is used as an important aroma chemicals in perfume industries, food industries and also in compositions for weight loss with improved taste. Raspberry ketone was described for the first time as a characteristic component of Raspberry flavour (H. Schinz et. al. Helv. Chim. Acta. 1957, 40, 1839). However, this substance was already known in its natural state as a component of a polygonacaea. The proportion of raspberry ketone in the raspberry is only between 9 and 174 μg per kilogram of fresh fruit depending on the variety (W. Borejsza-Wysocki et. al. J. Food Chem., 1992, 40, 1176). Thus, the concentration of raspberry ketone in raspberry fruit is so low that extraction of the compound from the fruit would not be economically viable. Therefore, there is no practical natural source for isolation of such important aroma chemical.

Reference may be made to K. Krishnan et. al. Appl. Cata. A: General, 241 (2003) 247-260, wherein liquid phase alkylation of phenol (about 5 mole) with 4-hydroxybutan-2-one (about 1 mole) was carried out in presence of different types modified zeolite, H-beta zeolites and other solid catalysts for a period of 48-60 hours at 100° C. to produce raspberry ketone. The main drawback of the process is the selectivity which is less than 40%.

Reference may be made to D. Joulain et. al. U.S. Pat. No. 5,908,770, June 1999 wherein a microbiological preparation of 4-(4-hydroxyphenyl)butan-2-one has been described where a solution of 4-(4-hydroxyphenyl)but-3-en-2-one in ethanol at 96° C. was added very slowly over 10 minutes to a suspension of baking yeast in D-glucose at 35° C. and agitated the mixture for about 48 hours followed by continuous liquid-liquid extraction for about 12 hours using methyl-tertiary-butyl ether. After evaporating the liquid, a solid mass of crude product is obtained consisting mainly (GC-MS) about 56% of 4-(4-hydroxyphenyl)butan-2-one and 37% 4-(4-hydroxyphenyl)butan-2-ol. The product was then purified. The main drawback is that the process is time consuming and the selectivity is about 56% only.

Reference may be made to B. K. Osjek et. al. Tetrahedron, 59 (2003) 9517-9521 wherein efficient production of raspberry ketone from rhododendrol rac-2 (rhododendrol is produced in the inner bark of the stressed and drying branches of most white barked birch species by natural hydrolysis of glucoside rhododendrin) via "Green" biocatalyst oxidation has been described. The main drawback of the process is that the conversion is only 52% in 24 hours.

Friedel Crafts catalysis is one of the major industrially important processes that is widely used in the synthesis of low and high volume chemicals through acylations, benzylations, alkylations and sulphonylations giving a wide range of useful products like ketones, alcohols, alkyl aromatics and sulphones. Reference may be made to A. G. Badische et. al. Patent (German) 2145308 wherein raspberry ketone is commercially produced by alkylation of phenol with vinyl ketone or 4-hydroxybutan-2-one in presence of acid catalysts such as $H_2SO_4$, $H_3PO_4$ and HCl. Main drawback is that the catalysts are hazardous in nature and require replacement in view of environment pollution. The use of safe solid acids in the place of traditional Friedel Crafts catalysts and mineral acids have become important. Ecofriendly solid acid catalysts are rapidly emerging as a new and environment friendly materials. Attempts are being made to replace highly corrosive concentrated HCl, $H_2SO_4$, anhydrous $AlCl_3$ in F.C. alkylation reactions etc. by solid acid catalysts. All the solid acids are characterized by the presence of protons on the surface leading to Bronsted and/or Lewis acidity.

Reference may be made to P. Laszlo and A. Mathy; Helvetica Chimica Acta 70 (1987) 577 wherein Friedel-Crafts alkylation by using transition metal exchanged Montmorillonite K 10 was carried out for reactions like benzylation of benzene etc. No mention was made for preparation of 4-(4-hydroxyphenyl)butan-2-one.

Reference may be made to J. Org. Chem. 59, 1994, 5901, wherein Cation-exchanged Montmorillonite catalysed alkylation of phenol with 4-hydroxybutan-2-one to produce raspberry ketone was carried out at 100° C. for about 48 hours to produce 4-(4-hydroxyphenyl)butan-2-one. This paper also described several cation exchanged Montmorillonite clay catalysts. The main drawback of the process is that the selectivity (GC analysis) of the desired products is from 3 to 35%. The best catalyst (i.e., $Fe^{3+}$— Mont.) under the reaction conditions of temperature: 130±50° C.; pressure: 2±1 bar for a time duration of 24 hrs shows selectivity of only 47.54%.

OBJECTS OF THE INVENTION

The main object of the present invention is to provide solid acid catalysed Friedel-Crafts alkylation to produce 4-(4-hydroxyphenyl)butan-2-one which obviates the drawbacks of the hitherto known prior arts as detailed above.

Another object of the invention is to provide a process for the preparation of 4-(4-hydroxyphenyl)butan-2-one with about >75% selectivity and high conversion.

A further object of the invention is to provide a simple process for the preparation of 4-(4-hydroxyphenyl)butan-2-one which is to be carried out in a single step.

Yet another object of the present invention is to provide modified acid activated Montmorillonite clay catalyst. The modification of the clay is done by acid activation in order to get desired acidic porous siliceous materials to be used as solid acid catalyst as such for organic synthesis particularly for alkylation of phenols with 4-hydroxybutan-2-one to produce 4-(4-hydroxyphenyl)butan-2-one.

Still another object of the present invention is to provide preparation of acid activated Montmorillonite clay catalysts exhibiting layered clay structures (basal spacing $d_{001}$ ranging from about 10 to 13.5 Å), desired porosity (micro-5-15 Å and meso 30-80 Å), pore volume, acidity as well as surface area (>250 m$^2$/g) for applying as improved solid acid catalysts in Friedel-Crafts alkylation reactions.

Still another object of the present invention is to provide a highly selective Friedel-Crafts alkylation reaction of phenol with 4-hydroxybutan-2-one to produce 4-(4-hydroxyphenyl)butan-2-one.

Still another object of the present invention is to provide a benign Friedel-Crafts alkylation reaction of phenol with 4-hydroxybutan-2-one to produce 4-(4-hydroxyphenyl)butan-2-one.

Still another object of the present invention is to provide a clean, inexpensive and consistently recyclable efficient solid acid catalyst for Friedel-Crafts alkylation reaction of phenol with 4-hydroxybutan-2-one to produce 4-(4-hydroxyphenyl)butan-2-one.

The above and other objects of the invention are achieved by preparing 4-(4-hydroxy phenyl)butan-2-one from phenol and 4-hydroxybutan-2-one with >75% (maximum up to 81%) selectivity, using solid acid catalysts.

SUMMARY OF THE INVENTION

Accordingly the present invention provides an acid activated (HCl) solid acid catalyst Montmorillonite comprising of layered clay structures (basal spacing $d_{001}$ ranging from about 10 to 13.5 Å), highly porous {micropore in the range 5 to 15 Å and mesopore in the range 30 to 80 Å}, average pore volume 0.2 to 0.65 cc/g, surface acidity in the range 0.4-0.6 mmol/g and high surface area (250-400 m$^2$/g) siliceous layered matrix. Unmodified Montmorillonite clay does not show any catalytic activity.

In an embodiment of the invention the process for preparation of the solid acid catalysts wherein the steps comprising: leaching out the octahedral alumina from the purified Na-Montmorrillonite clay matrix by acid (e.g. HCl) treatment by (i) Purification of Montmorillonite clay by dialysis technique, (ii) Conversion into homoionic Na-Montmorillonite clay, (iii) treating homoionic Na-Montmorillonite clay with an acid (HCl) of concentration ranging between 1-4 M, for a period ranging between 5 minutes to 4 hours, at a refluxing temperature of about 100° C., (iv) purification by washing with distilled water to obtain the acid activated (HCl) solid acid catalyst Montmorillonite consists of layered clay structures (basal spacing $d_{001}$ ranging from about 10 to 13.5 Å), highly porous {micropore in the range 5 to 15 Å and mesopore in the range 30 to 80 Å}, average pore volume 0.2 to 0.65 cc/g, surface acidity in the range 0.4-0.6 mmol/g and high surface area (250-400 m$^2$/g) siliceous layered matrix.

In another embodiment of the invention wherein the catalyst prepared is useful for the preparation of 4-(4-hydroxyphenyl)butan-2-one wherein the process for preparation of 4-(4-hydroxyphenyl)butan-2-one comprises: contacting phenol with 4-hydroxybutan-2-one under constant stirring in a mol ratio ranging 3:1 to 1:3 at a pressure ranging between 1-15 bar at temperature ranging between 100-150° C., for a period ranging between of 1-24 hours in presence of solid acid catalysts in the range 0.6 to 2.0 g such as acid activated-Montmorillonite clay composite wherein the acid activated (HCl) solid acid catalyst Montmorillonite consists of layered clay structures (basal spacing $d_{001}$ ranging from about 10 to 13.5 Å), highly porous {micropore in the range 5 to 15 Å and mesopore in the range 30 to 80 Å}, average pore volume 0.2 to 0.65 cc/g, surface acidity in the range 0.4-0.6 mmol/g and high surface area (250-400 m$^2$/g) siliceous layered matrix to obtain the compound 4-(4-hydroxyphenyl)butan-2-one.

In an embodiment of the invention wherein solid acid catalyst Montmorillonite prepared by modifying the Na-Montmorillonite with acid (HCl) treatment and activating the catalysts at about 120° C. for about 2 hours prior to applications.

In an embodiment of the invention wherein the selectivity of the Fridel Craft's alkylation of phenol with 4-hydroxybutan-2-one to produce 4-(4-hydroxyphenyl)butan-2-one (Raspberry ketone) catalysed by the modified Montmorillonite clay mineral is high (>75%).

In an embodiment of the invention wherein the conversion of the Fridel Craft's alkylation of phenol with 4-hydroxybutan-2-one to produce 4-(4-hydroxyphenyl)butan-2-one (Raspberry ketone) catalysed by the modified Montmorillonite clay mineral is in the range of 35-55%.

In an embodiment of the invention wherein the solid acid catalysts prepared are of high purity, eco-friendly and inexpensive.

DETAILED DESCRIPTION OF THE INVENTION

Accordingly the present invention provides a modified clay catalysed alkylation process to produce 4-(4-hydroxyphenyl)butan-2-one which comprises of contacting phenol with 4-hydroxybutan-2-one under constant stirring and at pressure of 1-15 bar at temperature 100-140° C. for a period of 1-24 hours in presence of solid acid catalyst such as acid activated-Montmorillonite clay composite prepared by modifying the Na-Montmorillonite with acid (HCl) treatment and activating at about 120° C. for about 2 hours.

In another embodiment of the invention, the selectivity to 4-(4-hydroxy phenyl)-butan-2-one is in the range of 75-81%.

In another embodiment of the invention, the catalyst used is a solid acid catalyst comprising acid activated Montmorillonite clay prepared by modifying the Na-Montmorillonite with mineral acid (HCl) treatment and activating at about 100-120° C. for about 6-12 hours.

In another embodiment of the invention, the molar ratio of phenol to 4-hydroxybutan-2-one is in the range between 3:1 and 1:3.

In another embodiment of the invention, the reaction time of alkylation is in the range of 12-24 h.

In another embodiment of the invention, alkylation is effected at a temperature in the range of 100-140 degree C.

In another embodiment of the invention, alkylation is effected at a pressure in the range of 1-15 bar.

In an embodiment of the present invention, a process of purification of the Montmorillonite clay has been described as • About 60 g of Montmorillonite clay [M/S Gujarat Mines Bentonite, Gujarat, India, exhibiting Cation Exchange Capacity (CEC) 130 meq/100 g clay determined by standard technique and evaluated by XRD as: Oriented films for the study were prepared from Na-Montmorillonite on glass slides by allowing a few drops of suspension of the clay in water and then dried at room temperature. The basal spacings ($d_{001}$) at room temperature as determined by XRD technique were found to around 12.5 Å. The slides were kept over ethylene glycol in closed desiccator for about 24 hours and the basal spacing ($d_{001}$) was found to be about 16.5 Å characteristic for Montmorillonite clay mineral was added under constant stirring to about 3000 ml distilled water in 5000 ml beaker and then allowed to settle for about 20 hours and the slurry collected from 18 cm from the top of the surface in order to collect less than 2 µm fraction particle size reach in Montmorillonite clay mineral was dried at 50±5° C. in air oven to get solid mass.

In another embodiment of the present invention, a process for conversion into Na-Montmorillonite has been described as: About 2 g of dry purified Montmorillonite clay was suspended into 100 ml of distilled water and to it 100 ml of 2 M NaCl solution was added and kept stirring for about 2 hours. The mass was allowed to settle and the supernatant liquid was decanted off. The slurry was again treated with 2 M NaCl solution and stirred. This step was repeated for about four times. The excess NaCl was removed by dialysing the residue against distilled water till the conductivity of dialyzate approached that of distilled water and showed negative test for chloride ion with silver nitrate. The mass was then dried at 50±5° C. in air oven.

In yet another embodiment of the present invention, a process for preparation of acid activated Montmorillonite has been described in order to prepare micro- (<20 Å) and mesoporous (20-500 Å) aluminosilicate from Montmorillonite clay minerals containing mainly octahedral and tetrahedral aluminum in the framework. The process comprises mixing the clay mineral with desired acid to leach substantially the octahedral aluminum while leaving preferably the tetrahedral aluminum. The process has been described as: In a round bottom flask, 5 gm of Montmorillonite clay was taken and to it 200 ml of 1-4 M HCl was added. The mixture was refluxed at 100° C. for a period 5 minutes to 4 hrs. After cooling down the mixture to room temperature, the slurry was filtered through Whatman 41 filter paper and the residue was washed with distilled water till it becomes acid free. The clay was then dried in air oven at 50-60° C. for about 24 hrs. Almost white powder product was obtained. Yield 90.2%.

In still another embodiment of the present invention, a process has been described for preparation of layered clay structures (basal spacing $d_{001}$ ranging from about 10 to 13.5 Å) high surface area (BET) in the range of 250 to 400 m$^2$/g, a pore volume in the range of 0.4 to 0.8 cc/g, and a pore diameter in the range of 5-80 Å and acidities in the range of 0.3-0.6 mmol/g from Montmorillonite clay by acid activation in order to use as solid acid catalyst for Friedel-Crafts alkylation reactions.

In still another embodiment of the present invention, the parameters of the catalytic reactions is described as: In a 150 ml capacity Teflon coated pressure reactor (Make Berghof, Model HR 100, Germany) equipped with stirring attachment and temperature controller, the reactants such as phenols (1-3 mol) and 4-hydroxybutan-2-one (1-3 mol) in different mol ratios are taken. The desired quantity of the catalyst (Acid activated Montmorillonite) was introduced into the reactor. The reaction was carried from 1-24 hours under a pressure of 1-15 bar in the temperature range 100-140° C. The products were analysed by GC (Chemito Model GC-1000).

Scientific Explanation of the Activities and Mechanism of the Reactions:

Montmorillonite clay mineral, a member smectite group of clay, is a hydrated 2:1 layered dioctahedral aluminosilicate. It is composed of two tetrahedral silicate sheets bonded to either side of an octahedral aluminate sheet. Isomorphous substitution of $Mg^{2+}$ for the octahedral aluminium, and of $Al^{3+}$ for the tetrahedral silicon, results in charge deficit, which is balanced by hydrated exchangeable cations like $Na^+$ or $Ca^{2+}$ and occupy the surfaces between clay layers. Such clays after acid activation may exhibit both Bronsted and Lewis acidity. Both Bronsted and Lewis acidities play a vital role in the catalytic activity. Acid activation i.e. leaching treatment of Montmorillonite, in general, increase 4-5 fold in the acidity of the clay. Montmorillonite after washing with mineral acids has surface acidities in between that of concentrated nitric and sulfuric acids.

Acid activation of Montmorillonite clay results several significant possible changes in the structure such as: (i) Exchange of the interlayer cations with $H^+$, (ii) Delamination of individual clay platelets into different aggregated states, (iii) Dissolution of the individual clay platelets and (iv) Generation of poorly crystalline and highly porous siliceous phase. The extent of acid-treatment has profound implications for the use of Montmorillonite clay as acid catalysts. Dissolution of the clay and formation of hydrous, amorphous, silica-rich phases in part, promote the catalytic activity of the acid-treated material for either Bronsted and Lewis acid catalysed reactions. The catalytic activities of Montmorillonite clay (consisting of aluminosilicate) is mainly based on its acidities related directly to various aluminium sites. It is known that a tetrahedral aluminum site generates Bronsted acidity while an octahedral aluminum site is usually connected to Lewis acidity. Acid leaching of Montmorillonite clay lead to depopulate the octahedral sheet and consequently reduces the original cation exchange capacity of the clay. Thus as the extent of acid leaching increases the cation exchange capacity of the clay reduces. However, with increasing acid concentration and treatment time, large amount of octahedral alumina are removed leading to a decrease in the Lewis acidity. Acid treated montmorillonite commercially known as K10-montmorillonite which has predominant Bronsted acid sites. Most current commercial Montmorillonite acid activation processes use $H_2SO_4$. K-10 montmorillonite is used as a catalyst in organic synthesis. Specifically, K-10 montmorillonite is widely considered to be a green heterogeneous catalyst. On progressing the time of acid 4M HCl treatment, the acidity generated are about 0.4 to 0.6 mmol/g for 1 to 4 hours treatment.

The XRD pattern of the untreated Montmorillonite clay shows highly intense basal peak at about $2\theta=6.65°$ corresponding to the basal d-spacing ($d_{001}$) of about 13.29 Å i.e. interlayer spacing of about 3.69 Å. During the acid activation, the intensity of the basal peak ($d_{001}$) starts depleting with increasing time of acid treatment and for 1-4 M HCl treatment from 5 minutes to 4 hours, the basal spacing value approaches to almost zero (basal spacing $d_{001}$ values ranging from about 10 to 13.5 Å) indicating delamination or destruction of the layer structure. Higher intensity basal reflections indicate a greater number of repeating clay platelets within the aggregate and lower intensity suggests depletion of layer stacking due to poorer orientation of clay platelets and dissolution of the clay platelets.

The FTIR spectra of the untreated Montmorillonite clay exhibits absorption bands at about 3625 and 1639 cm$^{-1}$ corresponding to stretching and bending vibrations of OH groups of Al—OH of the clay structure and also exhibits a broad band at about 3447 due to OH stretching of water molecules present in the interlayer region. The absorptions at 914, 877 and 834 cm$^{-1}$ are due to bending modes of the OH groups of AlOH, AlFeOH and AlMgOH respectively. Upon acid activation of Montmorillonite clay, the weakening and/or disappearing of most of the bands indicate partial of complete dissolution of Al, Fe and Mg from the clay structure. On progressing the time of acid 4M HCl treatment, the band at about 523 cm$^{-1}$ indicative for the presence of residual Al in the octahedral layer, gradually depletes and ultimately vanishes during about 4 hours treatment and thus corroborates the observation made by XRD study.

High surface area of Montmorillonite clay is directly related to the removal of aluminum in the structure. However, the maximum surface area is obtained only when the tetrahedral aluminum remains in the structure. A complete removal of aluminum leads to a destruction of some of the porosity. Acid-treatment has significantly reduced alumina content and increased the Si content. Untreated Montmorillonite clay is characterized by its single silicon peak at about −93 ppm ($Q^3(0Al)$) due to $SiO_4$ tetrahedra surrounded by three other silicate units in the tetrahedral sheet and one Al (or Mg) atoms through oxygen bridges of Montmorillonite clay. As time of the acid (HCl)-treatment increases, the peak i.e. −93 ppm ($Q^3(0Al)$) of Montmorillonite clay gradually disappear, and the new peaks at about −111 ppm [$Q^4(0Al)$ (Si—O—Si bond)] and −102 ppm [($SiO_3$)Si—OH bond] start appearing and intensifying and ultimately the only one intense peak remains i.e. −111 ppm ($Q^4(0Al)$(Si—O—Si bond) after prolong acid treatment. Therefore, $^{29}$Si MAS (Magic-Angle Spinning) NMR study indicates that the acid-treatment has almost completely changed the structure of Montmorillonite clay into amorphous silica. The $^{27}$Al MAS-NMR spectra of untreated Montmorillonite clay shows octahedrally (intense signal at 3.92 ppm) and tetrahedrally (weak signal at 66.25 ppm) coordinated alumina in the framework of the clay. The $^{27}$Al MAS-NMR spectra indicate that during acid activation, the intensity of the peaks due to octahedral Al decreases considerably along with shifting the peak position from 3.92 ppm to about 1.6 ppm for acid treatment period of up to about 4 hours, but the peak value at 67.43 ppm due to tetrahedral Al remains almost same similar to untreated clay indicating residual intact of the tetrahedral Al structure. Untreated Montmorillonite clay does not exhibit any active catalytic sites. Only after modification of the clay, catalytic activities are observed.

The acid (4 M HCl)-treatment for the period of 5 minutes to 4 hours, resulted surface area (BET) in the range 250 to 400 m²/g, average pore volume 0.2 to 0.65 cc/g and porosity i.e. micropore (<20 Å) in the range 10 to 15 Å and mesopore (20-500 Å) in the range 30 to 80 Å. The above characteristics of the modified Montmorillonite clay are likely to play a vital role in Friedel Crafts catalyzing reactions particularly acylation reactions.

The XRD, $^{29}$Si NMR and IR data provide evidence that the acid-leaching has fundamentally transformed the layered Montmorillonite into an amorphous silica-like structure. The resulting products, is no longer a Montmorillonite clay. The high surface area is related to the removal of most of the aluminum from octahedral sites in the clay. However, a maximum surface area is obtained only because of some or all the tetrahedra aluminum remains in the structure. A complete removal of aluminum leads to a destruction of some of the porosity.

Liquid phase alkylation of phenol with 4-hydroxybutan-2-one was carried out in presence of different types of solid acid catalysts show (Scheme-1) that the cleared para alkylated product 4-(4-hydroxyphenyl)butan-2-one was formed by direct C-alkylation of phenol and also by facile rearrangement of the O-alkylated and ortho alkylated products formed to the desired product under suitable reaction conditions. It is worth to mention here that the heats of formation of O-alkyl, para and ortho products are −58.7, −72.2 and −73.9 kcal/mol respectively and therefore; the heat of formation of O-alkylated product is about 13.5 kcal/mol higher than that of para alkylated product, the rearrangement of O-alkyl to para product is thus thermodynamically favourable.

Scheme-1

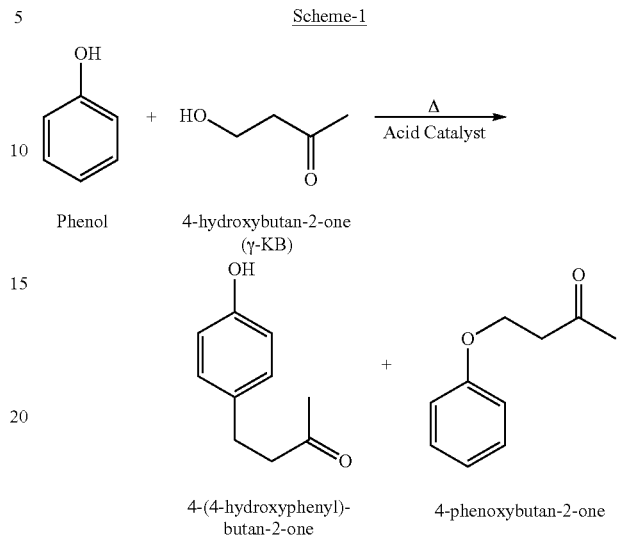

Phenol     4-hydroxybutan-2-one (γ-KB)

4-(4-hydroxyphenyl)-butan-2-one     4-phenoxybutan-2-one

The novelty of the present invention lies in the preparation of the solid acid catalysts by leaching out the octahedral alumina from the purified Na-Montmorrillonite clay matrix by acid (e.g. HCl) treatment under strictly controlled conditions such as strength of the acid and time of treatment in order to obtain desired characteristics of the catalysts through generating suitable basal spacing, high surface area, porosity (micro- and meso), pore volume, surface acidity etc. The preparative steps of the catalysts consist of (i) Purification of Montmorillonite clay by dialysis technique, (ii) Conversion into homoionic Na-Montmorillonite clay, (iii) Acid treatment under conditions such as (a) Strength of the acids 1-4 M, (b) time of treatment: about 5 minutes to 4 hours, (c) refluxing at about 100° C., and (iv) purification by washing. The novelty of the developed catalysts directly relates to (i) Suitable basal spacing (responsible for shape and size selectivity), (ii) High surface area and surface acidity (responsible for higher catalytic activities), (iii) Suitable porosity (responsible for size and shape selectivity of the catalytic reactions), and (iv) Suitable pore volume (responsible for higher yields of the catalytic reactions).

Without use of any catalyst, the yield of the desired product is almost negligible even after conducting the catalytic reactions for about 24 hours under the same experimental conditions.

The following examples are given by way of illustration of the working of the invention in actual practice and therefore should not be construed to limit the scope of the present invention.

EXAMPLE-1

About 60 g of Montmorillonite clay was added under constant stirring to about 3000 ml distilled water in 5000 ml beaker and then allowed to settle for about 20 hours and the slurry was collected from 18 cm from the top of the surface in order to collect less than 2 μm fraction particle size reach in Montmorillonite clay mineral was dried at 50±5° C. in air oven to get solid mass. About 2 g of dry purified clay was suspended into 100 ml of distilled water and to it 100 ml of 2 M NaCl solution was added and kept stirring for about 2 hours. The mass was allowed to settle and the supernatant liquid was decanted off. The slurry was again treated with 2 M NaCl solution and stirred. This step was repeated for about four times. The excess NaCl was removed by dialysing the residue against distilled water till the conductivity of dialyzate approached that of distilled water and showed negative test for chloride ion with silver nitrate. The mass was then dried at 50±5° C. in air oven. In a round bottom flask, 5 gm of Montmorillonite clay was taken and to it 200 ml of 4M HCl was added. The mixture was refluxed at 100° C. for different period like 5 minutes to 4 hrs. After cooling down the mixture to room temperature, the slurry was filtered through Whatman 41 filter paper and the residue was washed with distilled water till it becomes acid free. The clay was then dried in air oven at 50-60° C. for about 24 hrs. Yield about 90%. The acid (4 M HCl)-treatment for the period of 5 minutes to 4 hours, resulted in layered clay structures (basal spacing $d_{001}$ ranging from about 10 to 13.5 Å), surface area (BET) in the range 250 to 400 m$^2$/g, average pore volume 0.2 to 0.65 cc/g and porosity i.e. micropore (<20 Å) in the range 10 to 15 Å and mesopore (20-500 Å) in the range 30 to 80 Å. The catalyst must be activated at about 120° C. for about 2 hours before conducting the catalytic Friedel-Crafts alkylation reactions.

EXAMPLE 2

Acid treated (4 M HCl for 5 minutes) Montmorillonite clay was activated at 120° C. in an air oven for 2 hours and cooled in a desiccator at room temperature and then 2.00 g of the activated catalyst added to a mixture of 3.80 ml 4-hydroxybutan-2-one and 4 g of phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 39.6% and the selectivity of the desired compound was 79.89%.

EXAMPLE 3

Acid treated (4 M HCl for 15 minutes) Montmorillonite was activated at 120° C. in an air oven for 2 hours and cooled in a desiccator at room temperature and then 0.67 g of the activated catalyst added to a mixture of 1.25 ml 4-hydroxybutan-2-one and 4 g of phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 37.5% and the selectivity of the desired compound was 81.17%.

EXAMPLE 4

Acid treated (4 M HCl for 15 minutes) Montmorillonite was activated at 120° C. in an air oven for 2 hours and cooled in a desiccator at room temperature and then 1.06 g of the activated catalyst added to a mixture of 5.6 ml 4-hydroxybutan-2-one and 2 g phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 54% and the selectivity of the desired compound was 75%.

EXAMPLE 5

Acid treated (4 M HCl for 15 minutes) Montmorillonite was activated at 120° C. in an air oven for 2 hours and cooled in a desiccator at room temperature and then 2 g of the activated catalyst added to a mixture of 3.8 ml 4-hydroxybutan-2-one and 4 g of phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 45.22% and the selectivity of the desired compound was 77.2%.

EXAMPLE 6

Acid treated (4 M HCl for 2 hours) Montmorillonite was activated at 120° C. in an air oven for 2 hours and cooled in a desiccator at room temperature and then 2 g of the activated catalyst added to a mixture of 3.8 ml 4-hydroxybutan-2-one and 2 g of phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 48.22% and the selectivity of the desired compound was 74.57%.

EXAMPLE 7

Acid treated (4 M HCl for 2 hours) Montmorillonite was activated at 120° C. in an air oven for 2 hours and cooled in a desiccator at room temperature and then 2 g of the activated catalyst added to a mixture of 3.8 ml 4-hydroxybutan-2-one and 4 g of phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 39.6% and the selectivity of the desired compound was 75.78%.

EXAMPLE 8

Acid treated (4 M HCl for 4 hours) Montmorillonite was activated at 120° C. in an air oven for 2 hours and cooled in a desiccator at room temperature and then 2 g of the activated catalyst added to a mixture of 3.11 ml 4-hydroxybutan-2-one and 2.8 g phenol in a pressure reactor fitted with stirring arrangement and temperature controlling system. The reaction was carried out at pressure 2±1 bar at temperature 130±5° C. for a period of 24 hours at 500 rpm. GC analysis showed conversion about 47.9% and the selectivity of the desired compound was 75.6%.

EXAMPLE 9

Acid treated (4 M HCl for 5 minutes) Montmorillonite was activated at 120° C. in an air oven for 2 hours and cooled in a desiccator at room temperature and then 2.0 g of the activated catalyst added to a mixture of 3.8 ml 4-hydroxybutan-2-one and 4 g phenol in a pressure reactor fitted with stirring arrangement and temperature controlling system. The reaction was carried out at pressure 12±3 bar at temperature 145±5° C. for a period of 24 hours at 500 rpm. GC analysis showed conversion about 39.6% and the selectivity of the desired compound was 79.9%.

EXAMPLE 10

Acid treated (4 M HCl for 15 minutes) Montmorillonite was activated at 120° C. in an air oven for 2 hours and cooled in a desiccator at room temperature and then 2.0 g of the activated catalyst added to a mixture of 3.8 ml 4-hydroxybutan-2-one and 4 g phenol in a pressure reactor fitted with stirring arrangement and temperature controlling system. The reaction was carried out at pressure 12±3 bar at temperature 145±5° C. for a period of 24 hours at 500 rpm. GC analysis showed conversion about 35.6% and the selectivity of the desired compound was 78.4%.

EXAMPLE 11

Acid treated (4 M HCl for 2 hours) Montmorillonite was activated at 120° C. in an air oven for 2 hours and cooled in a desiccator at room temperature and then 2.0 g of the activated catalyst added to a mixture of 3.8 ml 4-hydroxybutan-2-one and 4 g phenol in a pressure reactor fitted with stirring arrangement and temperature controlling system. The reaction was carried out at pressure 12±3 bar at temperature 145±5° C. for a period of 24 hours at 500 rpm. GC analysis showed conversion about 39.6% and the selectivity of the desired compound was 75.8%.

The main advantages of the present invention are:
1. A novel and eco-friendly process for the production of an commercially important aroma compound 4-(4-hydroxyphenyl)butan-2-one.
2. The present invention is distinguished from the prior art in that the process is highly selective (>75% and up to 81%) with good yield 35-55%).
3. The alkylation process of the present invention is simple and involve single step.
4. The present invention utilizes a clean and inexpensive clay based solid acid catalyst.
5. The present invention utilizes a reusable catalyst with consistent activity.
6. The present invention provides a clean process.
7. Separation of the catalyst from the reaction mixture is easy
8. Disposal of the solid acid catalysts is not a problem since they are environmentally

We claim:

1. A solid acid catalyst obtained by:
    (i) modifying Na-Montmorillonite with acid treatment, and
    (ii) activating the obtained product at 120° C. for 2 hours.
2. The solid acid catalyst of claim 1 comprising layered clay structures with:
    basal spacing $d_{001}$ ranging from about 10 to 13.5 Å;
    micropores in the range of 5 to 15 Å, mesopores in the range of 30 to 80 Å, and a pore volume 0.2 to 0.65 cc/g;
    surface acidity in the range of 0.4-0.6 mmol/g; and
    surface area of 250-400 $m^2$/g siliceous layered matrix.
3. A process for preparation of the solid acid catalyst of claim 1 comprising the steps of:
    (i) purifying Montmorillonite clay by dialysis;
    (ii) converting the Montmorillonite into homoionic Na-Montmorillonite clay;
    (iii) treating the homoionic Na-Montmorillonite clay with an acid of concentration ranging between 1-4 M, for a period ranging between 5 minutes to 4 hours, at a refluxing temperature of about 100° C;
    (iv) washing with distilled water to obtain the solid acid catalyst which consists of layered clay structures with basal spacing $d_{001}$ ranging from 10 to 13.5 Å, micropores in the range 5 to 15 Å, mesopores in the range of 30 to 80 Å, a pore volume in the range of 0.2 to 0.65 cc/g, a surface acidity in the range of 0.4-0.6 mmol/g and a surface area of 250-400 $m^2$/g siliceous layered matrix; and
    (v) activating at about 120° C. for about 2 hours.
4. A process for preparation of 4-(4-hydroxyphenyl)butan-2-one comprising contacting phenol with 4-hydroxybutan-2-one under constant stirring in a molar ratio ranging from 3:1 to 1:3, at a pressure ranging between 1-15 bar, at temperature ranging between 100-150° C., for a period of 1-24 hours, in the presence of the solid acid catalyst of claim 2 to obtain 4-(4-hydroxyphenyl)butan-2-one.
5. The process of claim 4, wherein the selectivity of Friedel-Crafts alkylation of phenol with 4-hydroxybutan-2-one to produce 4-(4-hydroxyphenyl)butan-2-one (Raspberry ketone) catalyzed by the catalyst of claim 1 is >75%.
6. The process of claim 4, wherein conversion of Friedel-Crafts alkylation of phenol with 4-hydroxybutan-2-one to produce 4-(4-hydroxyphenyl)butan-2-one (Raspberry ketone) catalyzed by the catalyst of claim 1 is in the range of 35-55%.
7. The solid acid catalyst of claim 1, which has an amorphous silica-like structure.
8. The solid acid catalyst of claim 1, wherein step (i) comprises treating Na-Montmorillonite clay with an acid of concentration ranging between 1-4 M for a period ranging between 5 minutes to 4 hours, at a refluxing temperature of 100° C.
9. The solid acid catalyst of claim 8, wherein the acid is hydrochloric acid.
10. The process of claim 3, wherein the acid is hydrochloric acid.
11. The process of claim 4 further comprising contacting phenol with 4-hydroxybutan-2-one under constant stirring in a molar ratio ranging 3:1 to 1:3, at a pressure ranging between 1-15 bar, at a temperature ranging between 100-150° C., for a period ranging between 1-24 hours, in the presence of a solid acid catalyst in an amount of 0.6 to 2.0 g, which solid acid catalyst consists of layered clay structures with basal spacing $d_{001}$ ranging from 10 to 13.5 Å, with micropores in the range 5 to 15 Å, mesopores in the range 30 to 80 Å, a pore volume in the range of 0.2 to 0.65 cc/g, surface acidity in the range 0.4-0.6 mmol/g, and a surface area of 250-400 $m^2$/g siliceous layered matrix, to obtain 4-hydroxybutan-2-one.

* * * * *

UNITED STATES PATENT AND TRADEMARK OFFICE
CERTIFICATE OF CORRECTION

PATENT NO. : 8,471,068 B2
APPLICATION NO. : 12/934568
DATED : June 25, 2013
INVENTOR(S) : Dipak Kumar Dutta et al.

It is certified that error appears in the above-identified patent and that said Letters Patent is hereby corrected as shown below:

In the Claims:

In claim 1, column 11, line 42, delete "C." and insert -- C -- therefor.

In claim 3, column 12, line 13, delete "C." and insert -- C -- therefor.

In claim 4, column 12, line 18, delete "C." and insert -- C -- therefor.

In claim 11, column 12, line 44, delete "C." and insert -- C -- therefor.

Signed and Sealed this
Tenth Day of September, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,471,068 B2 | Page 1 of 1 |
| APPLICATION NO. | : 12/934568 | |
| DATED | : June 25, 2013 | |
| INVENTOR(S) | : Dutta et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this
Tenth Day of February, 2015

Michelle K. Lee
*Deputy Director of the United States Patent and Trademark Office*